United States Patent [19]
Lankford

[11] Patent Number: 5,682,199
[45] Date of Patent: Oct. 28, 1997

[54] VIDEO ENDOSCOPE WITH INTERCHANGEABLE ENDOSCOPE HEADS

[75] Inventor: James D. Lankford, St. Louis, Mo.

[73] Assignee: Jedmed Instrument Company, St. Louis, Mo.

[21] Appl. No.: 621,712

[22] Filed: Mar. 28, 1996

[51] Int. Cl.[6] .............................. H04N 7/18; H04N 5/225
[52] U.S. Cl. .................... 348/72; 348/65; 128/4; 362/32
[58] Field of Search ......................... 348/66, 72, 75, 348/77, 65; 600/112, 173; 358/98; 362/32; 128/4; H04N 7/18, 5/225

[56] References Cited

U.S. PATENT DOCUMENTS

| | | |
|---|---|---|
| 4,590,923 | 5/1986 | Watanabe . |
| 4,601,284 | 7/1986 | Arakawa et al. . |
| 4,807,594 | 2/1989 | Chatenever . |
| 4,851,866 | 7/1989 | Ciarlei et al. . |
| 4,858,001 | 8/1989 | Milbank et al. . |
| 4,860,094 | 8/1989 | Hibino et al. . |
| 4,867,137 | 9/1989 | Takahashi . |
| 4,901,142 | 2/1990 | Ikuno et al. . |
| 4,947,245 | 8/1990 | Ogawa et al. . |
| 4,974,580 | 12/1990 | Anapliotis . |
| 4,998,182 | 3/1991 | Krauter et al. . |
| 5,005,943 | 4/1991 | Fort . |
| 5,061,995 | 10/1991 | Lia et al. ........................ 358/98 |
| 5,101,468 | 3/1992 | Chiu ............................. 385/115 |
| 5,124,797 | 6/1992 | Williams et al. . |
| 5,125,394 | 6/1992 | Chatenever et al. . |
| 5,156,141 | 10/1992 | Krebs et al. .................... 128/4 |
| 5,309,330 | 5/1994 | Pillers et al. .................... 362/32 |
| 5,341,240 | 8/1994 | Broome . |
| 5,363,839 | 11/1994 | Lankford . |
| 5,498,230 | 3/1996 | Adair ............................ 600/112 |

Primary Examiner—Tommy P. Chin
Assistant Examiner—Nhon Thanh Diep
Attorney, Agent, or Firm—Haverstock, Garrett & Roberts

[57] ABSTRACT

A video endoscopes with interchangeable endoscope heads which enables the operative hook up or connection of any of a variety of interchangeable endoscope heads including optical or objective elements for receiving and transmitting images of an object or target to be examined with both a video camera head and a light source in a single, quick and easy step. When operatively connected, the present video endoscope allows the optional simple and easy rotation of the endoscope head and light source relative to the video camera head to achieve a desired endoscope head orientation, and rotation of just the video camera head alone to adjust the orientation of the image viewed through the device on a video monitor or other medium.

18 Claims, 3 Drawing Sheets

VIDEO ENDOSCOPE WITH INTERCHANGEABLE ENDOSCOPE HEADS

The present invention relates generally to video endoscopes with interchangeable endoscope heads including optical or objective elements for receiving and transmitting images of an object or target to be examined, and, more particularly, to a video endoscope that enables the operative hook up or connection of any of a variety of interchangeable endoscope heads with both a video camera head and a light source in a single, quick and easy step. Further, when operatively connected, the present video endoscope allows simple and easy, virtually unlimited rotation of the endoscope head and light source relative to the video camera head to achieve a desired endoscope head orientation, and rotation of just the video camera head alone to adjust the orientation of the image viewed through the device on a video monitor or other medium.

BACKGROUND OF THE INVENTION

Video endoscopy is commonplace in both operating rooms and physician's offices for diagnosing and treating various conditions internal to the body. Telemedicine, wherein a video endoscopic examination or treatment is conducted at one location and the video image of the examination or treatment is transmitted via video link to another location, is an example of one of the more important applications for video endoscopy. During the course of a video endoscopic examination or treatment, endoscopes having objective elements with several different optical capabilities or characteristics may be required. For instance, endoscopes having different lengths, diameters, viewing angles, flexibility, and/or other special capabilities are available and may be necessary for the complete diagnosis and/or treatment of conditions in related regions of the body such as the ears, sinuses and throat. Also, endoscopes should be changed before insertion into new regions of the body to prevent the transfer of contaminants such as blood borne pathogens including virus, bacteria, and the like to the new regions. Still further, it is desirable to have the ability to rotate the objective element relative to the video camera or video pick up device to achieve a desired view of an object to be examined, and the ability to rotate the orientation of the image as viewed on a video monitor or other medium to facilitate diagnosis and treatment and comparison to other images. Numerous prior art video endoscopic devices having interchangeable objective elements or endoscope heads are known. See, for instance, the devices disclosed in U.S. Pat. Nos. 4,590,923; 4,601,284; 4,860,094; and 5,124,797. These known video endoscope devices are limited, however, in that they variously require multiple steps to operatively connect a video camera or other video pick up device and means for communicating light to the respective objective elements or endoscope heads. This can be a significant shortcoming when time is of the essence such as during emergency treatment and/or diagnosis, when a patient is experiencing discomfort, and when the cost of treating or consulting physicians' time and video link time are of concern. Various of such known devices also provide only limited image rotation capability beyond the capability to rotate the entire endoscope in a body cavity. Reference U.S. Pat. No. 4,858,001, which discloses a modular endoscopic apparatus with image rotation. This device is limited, however, in that it requires the video camera to be mounted in the distal end of an elongated rotatable shaft, which is a shortcoming for several reasons, including the requirement that the camera shaft be rotatable no more than about one revolution within its housing to avoid breakage of the wires connecting the camera to a video system, and the potential for contamination of internal regions of the shaft housing when the shaft is rotated.

OBJECTS OF THE INVENTION

It is therefore a principal object of the present invention to decrease the time, patient discomfort, and inconvenience associated with changing the objective elements of video endoscopes.

Another object of the invention is to provide a video endoscope that allows simpler, quicker, and easier hook-up of a light source and a video camera or video pick up device to an endoscope objective element.

Another object is to provide a video endoscope having a simpler, easier, more versatile image rotation capability.

Another object is to provide a video endoscope with an image rotation capability that is less prone to wiring and contamination problems.

Another object is to provide a single video endoscope system that achieves all of the above objects.

These and other objects and advantages of the present invention will become apparent after considering the following description of the invention and accompanying drawings.

SUMMARY OF THE INVENTION

In accordance with the above objects, the present invention overcomes many of the shortcomings and limitations associated with known video endoscopic devices by teaching the construction and operation of a video endoscope that enables the interchangeable operative hook up or connection of endoscope heads including a wide variety of optical or objective elements to both a video camera or other video pick up device and a light source in a single, quick and easy step. Additionally, the present invention provides the optional capability of easy relative rotation between the video camera and an operatively connected endoscope head and light source to enable viewing different objects and/or the orientation of the image seen through the camera without such problems as damage to the wires connected to the camera, or the possibility of additional contamination of the camera housing.

According to one preferred embodiment, the present video endoscope includes at least one endoscope head having an objective element for receiving and transmitting an image of an object to be examined and a light conductive element which serves as a conduit for receiving light from a light source and emitting the light for illuminating the object. The video endoscope has a video camera head including a video camera or video pick up device, the video camera head being adapted to be mounted to the endoscope head to allow relative rotation of the video camera head and the endoscope head with the video camera positioned to receive the image transmitted by the objective element. Also importantly, the video endoscope includes a member adapted to receive light from a light source and emit the light mounted for rotation about the video camera head in position to communicate light to the light conductive element when the video camera head is mounted to the endoscope head.

The preferred light emitting member is a fiber optic cable of conventional construction formed of a plurality of generally parallel light conductive fibers or filaments. The fiber optic cable includes a first or receptor end for receiving light from a light source such as an electric bulb, and a second or emitter end for emitting the light. Importantly, the emitter end of the fiber optic cable is held or carried by the video camera head in a position and orientation such that as the video camera head is mounted to a selected endoscope head, the emitter end of the fiber optic cable can also be brought into operative position to communicate light to the light receiving portion of the light conductive element which is positioned at a fixed, predetermined location on the endoscope head for that purpose. Because the fiber optic cable is held or carried by the video camera head in this manner, any need for separate means to couple or attach a fiber optic cable on each endoscope head is eliminated, as is a separate step or action to accomplish the attachment of the cable to the endoscope head and detachment of the cable after use. This is an important operational feature of the present invention as it results in a significant time savings when preparing the video endoscope for use, particularly when several endoscope heads are required.

An additional important feature of the preferred embodiment is the optional rotatability of the light emitting member relative to the video camera head. Although not required in all cases, this capability is desirable as it allows rotation of the endoscope head relative to the video camera head to facilitate the image selection and rotation capability of the endoscope. The rotatability of the light emitting member can be accomplished utilizing any suitable mounting member or holder that allows rotation of the light emitting member with the endoscope head while maintaining the light emitting member in the proper position and orientation for communicating light to the light conductive element of a selected endoscope head. The preferred mounting member or holder construction for use with the preferred fiber optic cable is a ring shaped member that mounts for rotational but no significant axial movement about an annular outer portion of the video camera head and which holds the emitter end of the fiber optic cable next to the video camera head in the required position. To hold the cable end, an internally threaded member adapted to receive and threadedly engage a conventional ACMI fitting on the emitter end of the fiber optic cable or other suitable means can be used. Alternatively, it is contemplated that the fiber optic cable could be mounted or held on the video camera head so as to communicate light to the endoscope head indirectly such as through a member that redirects the light at an angle or otherwise acts as an intermediate member for communicating the light to an attached endoscope head, as long as quick and easy attachment and the desired rotatability capabilities are still provided. Still further, as another alternative it is contemplated that the light source could be directly carried on the video camera head.

The light conductive element of the respective endoscope heads can include any member adapted to serve as a conduit for receiving light from the light emitting member and emitting the light to illuminate an object being examined. The preferred light conductive element is a bundle or strand of fiber optic filaments extending through a portion of the endoscope head and through the objective element between a light receptor end for receiving the light and a light emitter end for emitting the light. The preferred receptor end is a tubular member or post externally mounted to the endoscope head having an opening or aperture adapted for receiving a standard sized emitter end of a fiber optic cable.

The objective element of the respective endoscope heads each generally include a lens or lenses capable of receiving and transmitting an image of a desired object to be examined. The objective elements should have similar focal lengths for compatibility with the video camera head, but can otherwise differ extensively in characteristics such as rigidity, etc. Examples of suitable objective elements include the preferred objective elements which are elongated rod lenses such as those for examination of the nose, sinuses, throat, larynx, and ears, as well as other body cavities. The rod lenses can be adapted for headlong viewing, or can include mirrors for viewing at angles such as 30°, 60°, 70°, or 90° with respect to the longitudinal axis of the rod lens to provide an image viewing capability for inaccessible or hidden regions. Examples of other suitable objective elements include a fiber optic cable or other flexible or curved members capable of transmitting an image of an otherwise inaccessible or hidden region.

The video camera head can include any solid-state video camera or video pick up device suitable for receiving the visual image transmitted by the objective element and converting it to an electrical output data signal. For instance, the video camera head can include a high resolution color charge coupled device (CCD), a metal oxide silicone (MOS) image sensor, or a like device. Power to the camera and the output signal can be transmitted via a conventional video cable coupleable directly to the camera or video pick up device and to a video system that can include any of a variety of video processors and monitors, such as a high resolution color video monitor; a video recorder such as a video cassette recorder; a single image or multiple image format printer; and/or devices for transmitting the output signal to a remote location such as a cable or satellite system. The ability to couple a conventional video cable directly to the video camera is a desirable feature as it eliminates any need for intermediate wiring that may be prone to breakage and other problems.

Each endoscope head and the video camera head can include any suitable members cooperatively engageable to enable quickly removably mounting or connecting the video camera head to any of the endoscope heads. In the preferred embodiment, a quick release ball detent fitting and mating fitting is used, although it is contemplated that other fittings such as conventional bayonet type fittings and some screw type fittings could also be used. One important advantage of the preferred ball detent fitting is that it can be joined together in a simple, linear movement and allows smooth, easy relative rotation of the endoscope head and video camera head without looseness.

Other optional features of the present video endoscope include structure to enable sharply focusing the image received by the video camera or video pick-up device, for instance, by moving a focusing lens located in the image transmission path or by moving the camera itself, and a camera shield attachable in covering relation to the video camera or pick-up device to protect it from contamination, which shield is adapted to be disinfected and sterilized and/or disposed of after each use to prevent cross contamination of patients. For otoscopy, an endoscope head can include a fitting for mounting a speculum in overlaying relation to the rod lens or other objective element, and/or a fitting for attachment of an insufflator bulb thereto and associated internal passages for the communication of air under pressure to the interior of the speculum, as taught in my prior U.S. Pat. No. 5,363,839.

DETAILED DESCRIPTION OF THE PREFERRED EMBODIMENTS

Figure 1:
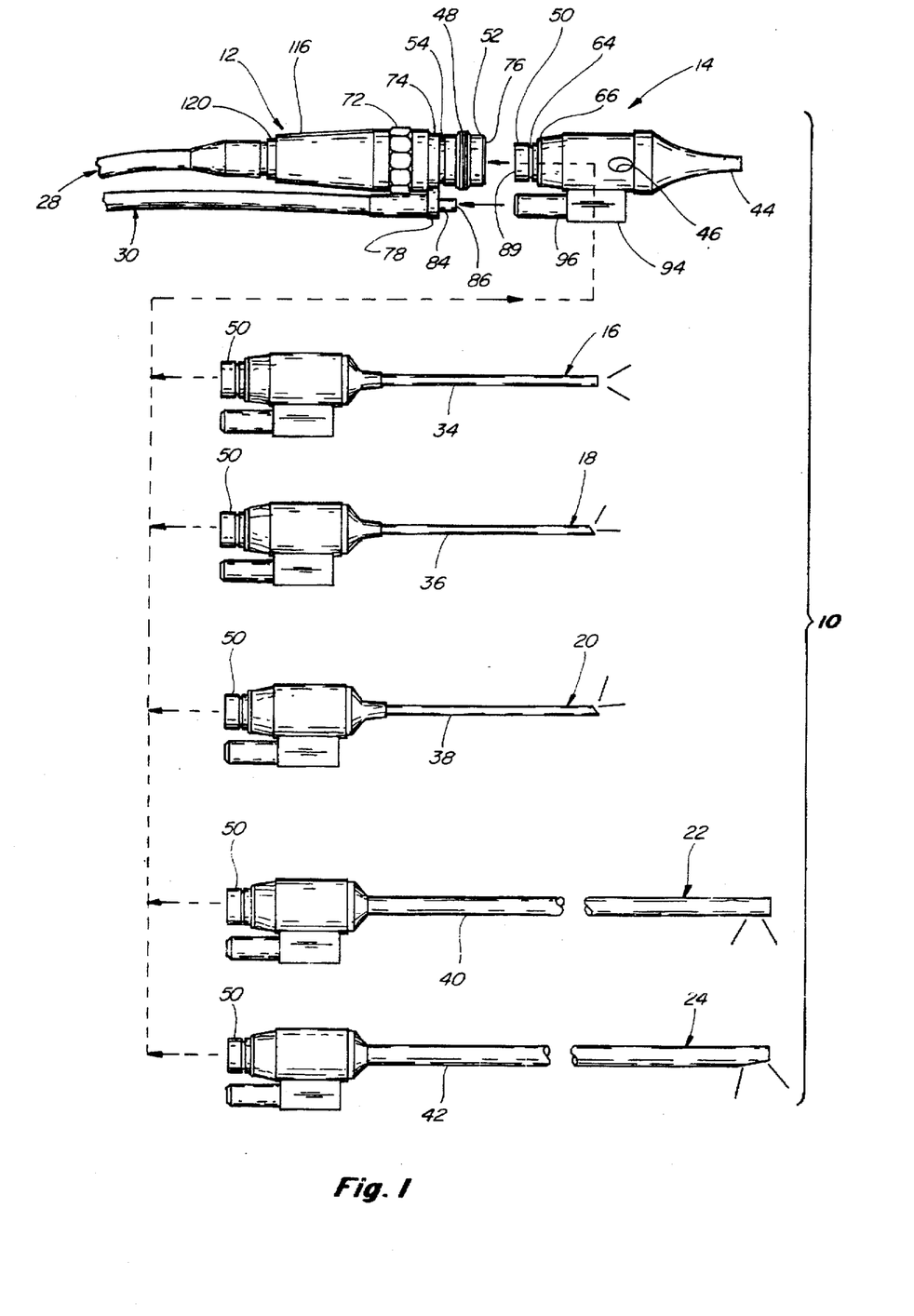
FIG. 1 is a side view of a video endoscope with interchangeable endoscope heads constructed according to the teachings of the present invention, the video endoscope including a video camera head containing a video camera (FIG. 6) with a video cable mounted thereto and an externally carried fiber optic cable, and a plurality of endoscope heads having different objective elements, the video camera head being interchangeably removably mountable to any of the endoscope heads in the manner shown.

Referring to the drawings more particularly by reference numbers, wherein like numerals refer to like parts, number 10 in FIG. 1 identifies a video endoscope with interchangeable endoscope heads constructed according to the teachings of the present invention. The present video endoscope 10 includes a video camera head 12 shown in position to be mounted to any of a plurality of endoscope heads identified by the even numbers between 14 and 24. Video camera head 12 contains a high resolution color video camera 26 (FIG. 6) which camera 26 is a CCD that can be operatively connected via a video cable 28 to a video system (not shown) capable of powering the camera and receiving the video output signal therefrom. The video system can include, for instance, a high resolution color video monitor; a video recorder such as a video cassette recorder; a video printer which can digitally store and reproduce any of the video frames on paper; and various cable or satellite transmission devices for communicating the video output signal of the camera to a remote location, all of which video items being well known in the art and widely commercially available. Importantly, video camera head 12 also carries a fiber optic cable 30 capable of receiving light from a light source (not shown) and communicating the light to a selected endoscope head 14-24 to which the video camera head 12 is mounted, as will be explained. As in the case of the video system just discussed, the light source operatively connected to fiber optic cable 30 can be any of a wide variety of commercially available units. Each endoscope head 14-24 includes an objective element for receiving or capturing the image of an object to be viewed and transmitting the image to video camera 26 of video camera head 12 when mounted to the endoscope head. The objective elements shown are various elongated rod lenses representative of a wide variety of those utilized for examining different portions of the body. In particular, endoscope 14 is an otoscope for the examination of the outer ear canal and ear drum which includes a rod lens 32 (FIG. 6) having dimensional characteristics suitable for insertion into the ear, including a length of about 34 millimeters (mm) and a diameter of about 2.7 mm. Endoscope heads 16–20 are different from endoscope head 14 in that they have rod lenses with dimensional characteristics suitable for insertion into the nose and sinus regions, endoscope 16 having a rod lens 34 adapted for headlong viewing, endoscope head 18 having a rod lens 36 adapted for viewing at a 30° angle with respect to the longitudinal axis of the rod lens, and endoscope head 20 having a rod lens 38 adapted for viewing at a 60° angle with respect to the axis of the rod lens. Endoscope heads 22 and 24 have rod lenses with dimensional characteristics suitable for insertion into the throat for examination of the larynx, rod lens 40 of endoscope head 22 being adapted for viewing at a 90° angle to the axis of the rod lens, and rod lens 42 of endoscope head 24 being adapted for viewing at a 70° angle to the axis of the lens. Referring again to endoscope head 14, since that endoscope head is for otoscopy, it includes a speculum 44 mountable in overlaying relation to rod lens 34 as shown to enable retracting or dilating the wall of the ear canal as speculum 44 and rod lens 34 are inserted therein, which speculum can be of conventional construction such as available from Welch Allyn Inc. of Skaneateles Falls, N.Y. Endoscope head 14 further includes a fitting 46 adapted to sealably receive a fitting 136 of a conventional insufflator bulb 134 (FIG. 9), which fitting 46 and an interior connecting passage 112 (FIG. 5) communicating fitting 46 with the interior of speculum 44 provide a conduit for the passage of air under pressure from the insufflator bulb to the interior of the speculum, the air under pressure being able to exit the speculum through an annular space around the distal end of rod lens 44 for demonstrating ear drum mobility as taught in my prior U.S. Pat. No. 5,363,839. The video camera head 12 when operatively connected to a video system and a light source is quickly and easily interchangeably mountable as explained next to any of the endoscope heads 14–24, to allow conducting a complete video examination of the outer ear canal and the ear drum, nose and sinuses, and throat and larynx.

Figure 2:
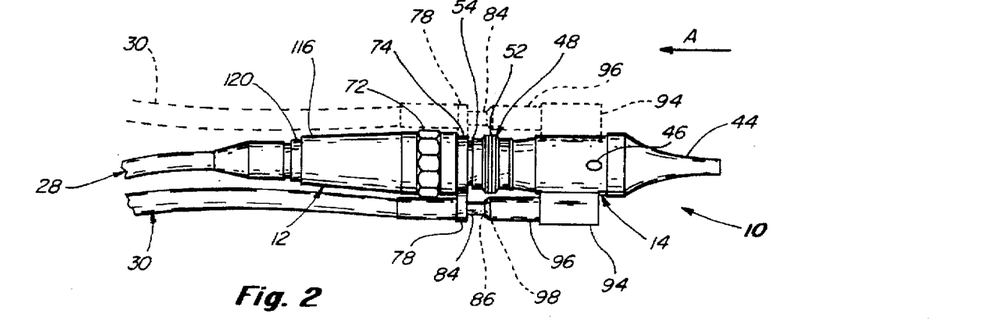
FIG. 2 is a side view showing the video camera head of FIG. 1 mounted to a selected one of the endoscope heads which is an otoscope, the otoscope having a speculum mounted in overlaying relation to the objective element thereof, the otoscope and fiber optic cable carried by the video camera head being shown in phantom rotated to an alternative position about the video camera head.

Referring also to FIG. 2, video camera head 12 can be quickly and easily mounted to any of endoscope heads 14–24 utilizing a ball detent fitting 48 located on the end of the video camera head hereinafter referred to as the front or forward end thereof. Ball detent fitting 48 is adapted to cooperatively receive and releasable engage a male fitting 50 on the rear end each of the endoscope heads 14–24. Ball detent fitting 48 includes an outer release ring 52 which is biased in the axial direction forwardly towards endoscope head 14 by one or more small internal springs (not shown). Outer release ring 52 is located in overlaying, concentric relation to a tubular member 54 of the video camera head, which tubular member 54 forms a forwardly facing cylindrical shaped receptacle 56 (FIG. 3) adapted for receiving the respective male fittings 50 on endoscope heads 14–24. Still referring to FIG. 3, tubular member 54 carries a plurality of ball detents 58 in radially spaced cavities located around receptacle 56, which cavities are defined by tapered or bell-shaped opposed side walls 60 that allow ball detents 58 to extend partially, but not completely, into receptacle 56.

Figures 3, 4, 5, 9:
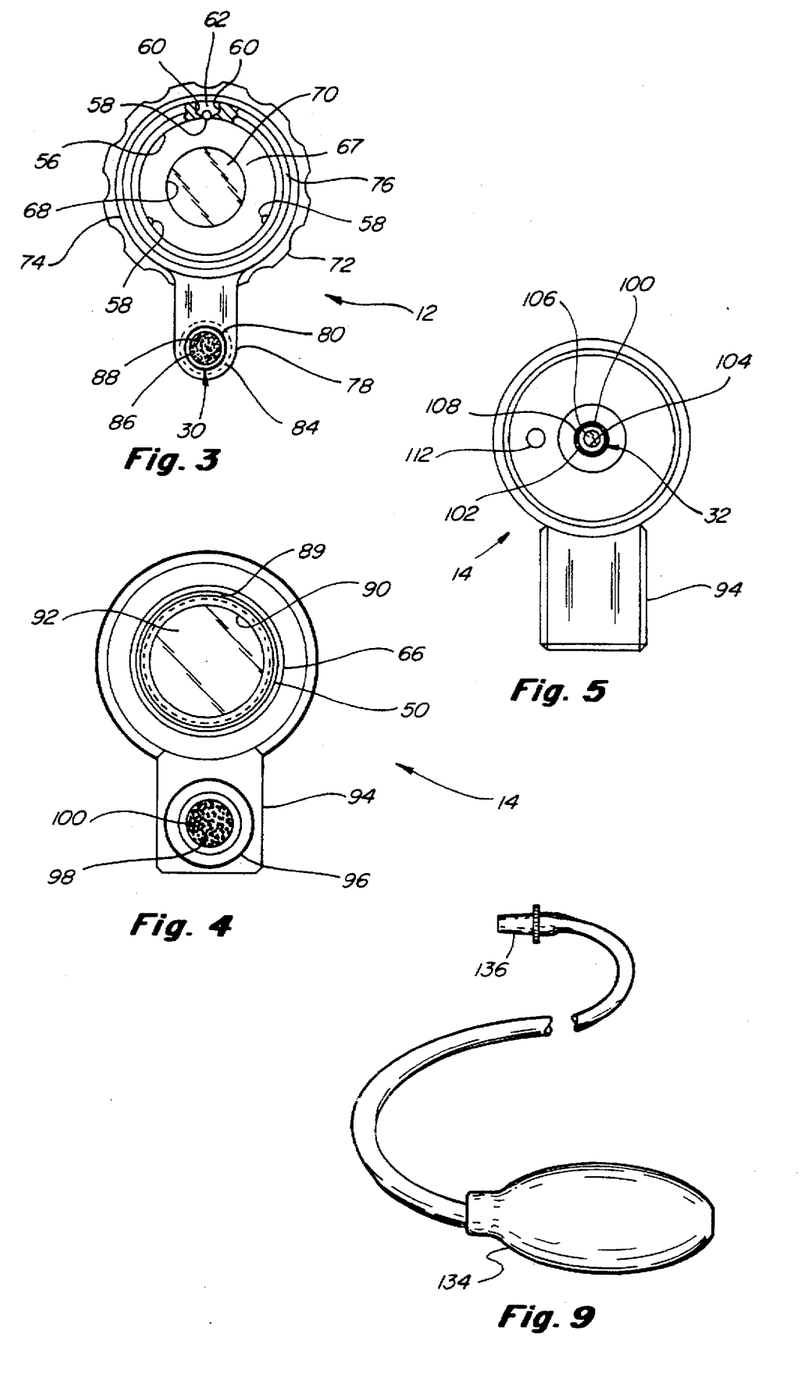
FIG. 3 is an enlarged front end view of the video camera head of FIG. 1 in partial cross-section to show a ball detent member thereof.
FIG. 4 is an enlarged rear end view of the otoscope head of FIG. 1 representative of the rear end of the other endoscope heads.
FIG. 5 is an enlarged front end view of the otoscope head of FIG. 1.
FIG. 9 is a side view of a typical prior art insufflator bulb for use with the otoscope of FIG. 1.

When outer release ring 52 is in the axial position shown in FIGS. 1 and 2, ball detents 58 are urged radially inwardly into receptacle 56 by an annular wedge surface 62 that extends around the inside of the release ring 52. Referring to FIG. 1, male fitting 50 includes an annular groove 64 extending therearound. Groove 64 is positioned and aligned to receive ball detents 58 when fitting 50 is fully received in receptacle 56 as shown in FIG. 2, to releasably secure video camera head 12 to a selected endoscope head such as the endoscope head 14 shown. To engage detents 58 with groove 64, release ring 52 is simply pulled back in the rearward direction indicated by the arrow identified by the letter A, and male fitting 50 of the selected endoscope head inserted fully into receptacle 56, then release ring 52 is released. This enables the internal springs to urge release ring 52 in the forward axial direction towards the endoscope head such that annular wedge surface 62 engages the ball detents which are thereby moved radially inwardly into engagement with annular groove 64 on the selected endoscope head to securely hold and prevent withdrawal of male fitting 50 of the endoscope head from receptacle 56. Here it should be noted that when video camera head 12 is securely mounted to a selected endoscope head utilizing ball detent fitting 48 and male fitting 50, those fittings allow relative rotation between the attached video camera head and endoscope head. Additionally, male fitting 50 of each respective endoscope head 14–24 includes an O-ring 66 extending therearound adjacent groove 64, which O-ring 66 is adapted to engage tubular member 54 of video camera head 12 to form a substantially air and moisture tight sealed condition between the video camera head and endoscope head, and which O-ring can also serve as an alternative stop for the engagement between the heads. When it is desired to change endoscope heads or otherwise remove video camera head 12 from the endoscope head, outer release ring 52 can be simply moved axially in the rearward direction indicated by the arrow A to release ball detents 58 and allow male fitting 50 to be withdrawn from receptacle 56.

Referring again to FIG. 3, video camera head 12 includes a rear wall 67 in receptacle 56 which serves as a stop for male fitting 50 when fully received in the receptacle. Rear wall 67 includes a centrally located aperture 68 therethrough, through which aperture 68 a lens 70 of video camera 26 can be seen. Camera 26 is located rearwardly of rear wall 67 and lens 70 is positioned to receive the image transmitted from an endoscope head to which the video camera head is mounted, which image can be focused by means of an external focusing barrel 72, as will be explained. Video camera head 12 importantly further includes a ring shaped member 74 mounted for rotational but not longitudinal movement in a groove or channel around tubular member 54 of video earnera head 12 at a predetermined longitudinal distance from forward end 76 of tubular member 54 (FIG. 1). Forward end 76 is located a known longitudinal distance from the rear wall 67 of receptacle 56, such that the longitudinal distance from ring member 74 to the rear wall of the receptacle and thus the longitudinal distance to an endoscope mounted to the video camera head is known. Ring shaped member 74 includes a sidewardly extending portion 78 having a threaded aperture 80 therethrough (FIG. 7) adapted for threadedly receiving a threaded mounting portion 82 (FIG. 6) on emitter end 84 of fiber optic cable 30. Emitter end 84 of fiber optic cable 30 includes an endmost tip portion 86 located a predetermined longitudinal distance from threaded mounting portion 82, which endmost tip portion 86 has a longitudinally facing opening to expose the terminal end of a bundle of fiber optic filaments 88 extending through cable 30. Because ring shaped member 74 is located a known distance from an attached endoscope and tip portion 86 is located a known distance from ring shaped member 74, the distance from tip portion 86 to a mating member on an attached endoscope will also be known.

FIG. 4 is a rear end view of endoscope head 14 showing male fitting 50 thereof, which is representative of the fittings 50 of the other endoscope heads 16–24. Male fitting 50 includes a rear end 89 (FIG. 1) that abuts rear wall 67 when received in receptacle 56, which rear end 89 has an aperture 90 containing an optically clear lens 92 through which an image received by rod lens 32 will be transmitted to the video camera. Endoscope head 14 includes a sidewardly extending light receptor post 94 which has a rearwardly extending tubular portion 96 (FIG. 1). Rearwardly extending tubular portion 96 includes a rearwardly facing aperture 98, which aperture 98 contains the terminal end of a bundle of fiber optic filaments 100 and mates with and receives the endmost tip portion 86 of fiber optic cable 30. Importantly for this purpose, the terminal end of fie bundle of fiber optic filaments 100 is desirably spaced or recessed into aperture 98 in the longitudinal direction by at least a distance sufficient to enable receipt of a portion of endmost tip portion 86 of fiber optic cable 30, tubular portion 96 containing aperture 98 is positioned radially with respect to the longitudinal axis of male fitting 50 correspondingly to the radial distance from tip end 86 of fiber optic cable 30 to the longitudinal axis of receptacle 56, and aperture 98 is located a predetermined longitudinal distance from rear end 89 of male fitting 50, such that when video camera head 12 is mounted to endoscope head 14, or any of the other endoscope heads 16–24, tip portion 86 can be inserted into aperture 98 with the same motion and at the same time: With tip portion 86 located in aperture 98, light from a light source operatively connected to the opposite end of fiber optic cable 30 (not shown) is communicated through the bundle of filaments 88 of cable 30 to the bundle of filaments 100 in the light receptor post. Also importantly, because ring shaped member 74 which holds fiber optic cable 30 to the video camera head is preferably rotatable axially thereabout, and the engagement between ball detent fitting 48 and male fitting 50 allows relative axial rotation of the video camera head and endoscope head, the endoscope head and fiber optic cable are axially rotatable together with respect to the video camera head, and, conversely, the video camera head is axially rotatable relative to the endoscope head and fiber optic cable, without loss of the ability to communicate light from cable 30 to the light receptor post of the endoscope head. This capability is important as it enables just the endoscope head and fiber optic cable to be rotated to thereby rotate the objective element of the endoscope head when inserted into a body cavity for viewing different regions of the body cavity, which is a feature that is particularly important when utilizing endoscope heads having angular viewing capabilities such as heads 18, 20 and 24. To illustrate, referring to FIG. 2, endoscope head 14 is shown in one rotational position with light receptor post 94 and rearwardly extending tubular portion 96, along with emitter end 84 of fiber optic cable 30 and ring shaped member 78 of the video camera head in solid lines, and in another rotational position 180 degrees opposite the first position in phantom lines. Also, with the endoscope head maintained at a constant angular orientation, just the video camera head can be rotated to change the orientation of the video image transmitted thereby.

FIG. 5 is a headlong view of the forward end of endoscope head 14 with speculum 44 removed to show distal end 102 of rod lens 32 and passage 112. Distal end 102 includes a central aperture 104 containing a lens 106 through which an image of an object to be examined is received, the image being communicated through rod lens 32 and transmitted therefrom through lens 92 at the rear end of endoscope head 14 (FIG. 4). Distal end 102 also includes an annular shaped aperture 108 extending around central aperture 104 in concentric relation thereto, which annular aperture 108 contains the other terminal end of fiber optic filament bundle 100. Light received by fiber optic filament bundle 100 through aperture 98 is communicated through the filaments and is emitted through annular aperture 108 to illuminate an object being examined in the conventional manner.

Figure 6:
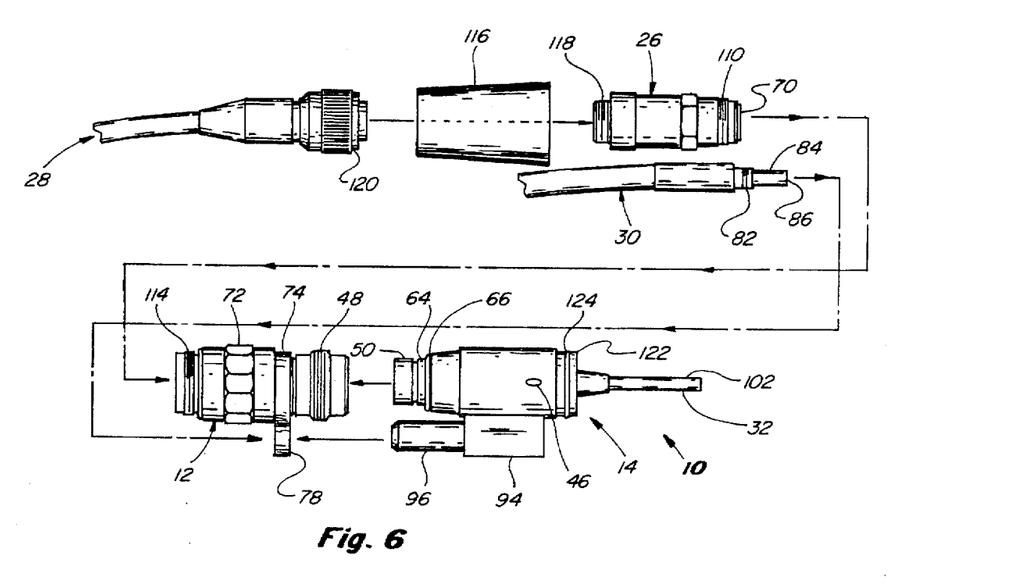
FIG. 6 is an exploded side view of the video camera head and the otoscope of FIG. 1, showing the various components of the video camera head and the speculum removed from the otoscope to show the rod lens thereof.

FIG. 6 is an exploded view of the complete endoscope with interchangeable heads 10 showing the various components thereof. In particular, ball detent fitting 48, focusing barrel 72, and ring shaped member 74 for holding fiber optic cable 30 are all located on video camera head 12. Video camera head 12 further includes a rearwardly facing internal cavity (not shown) adapted to at least partially receive video camera 26, which cavity includes an internal threaded member (not shown) threadedly engageable with external threaded portion 110 on video camera 26 and rotatable by focusing barrel 72 for moving the video camera axially in the video camera head for focusing an image received through lens 70. Since video camera 26 can extend rearwardly from video camera head 12 somewhat, to protect camera 26 from contamination and eliminate the need for sterilization thereof, video camera head 12 includes an external threaded end portion 114 adapted to threadedly engage and hold a tubular, frusto-conical shaped camera shield 116 in covering relation to the exposed portion of the camera. Camera shield 116 can be sterilized and reused after contamination or disposed of after use, as desired. The rear end of video camera 26 includes a conventional twelve pin video cable fitting 118 that plugs into a mating fitting 120 on the end of video cable 28 for operatively connecting camera 26 to a video system (not shown). When the video camera head is assembled, fitting 120 is at least partially contained within camera shield 116 (FIGS. 1 and 2) to protect it from contamination. The emitter end 84 of fiber optic cable 30 is shown including threaded mounting portion 82 and endmost tip portion 86. Endoscope head 14 is also shown, including post 94, tubular portion 96, male fitting 50, groove 64 and O-ring 66 on the rear end. Speculum 44 is removed from the forward end of endoscope 14 to show rod lens 32. Speculum 44 mounts to an annular portion 122 around the forward end of endoscope head 14 and a sealed condition is formed therebetween by O-ring 124 to prevent the escape of air under pressure therearound, as taught in my prior U.S. Pat. No. 5,363,839.

Figure 7:
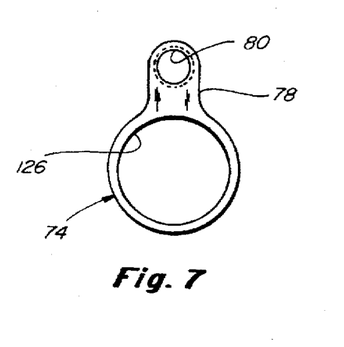
FIG. 7 is a front end view of a ring shaped member for carrying the fiber optic cable on the video camera head of FIG. 1.
Figure 8:
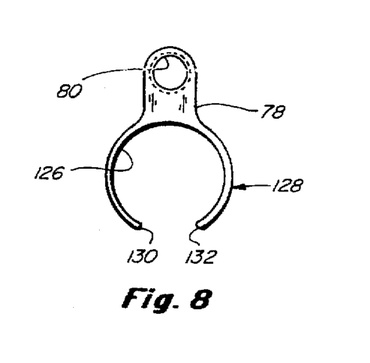
FIG. 8 is a front end view of an alternative embodiment of the member for carrying the fiber optic cable on the video camera head.

FIG. 7 is an end view of ring shaped member 74 showing a central aperture 126 therethrough adapted receive tubular member 54 of the endoscope head, and threaded aperture 80 on sidewardly extending portion 78 for receiving and holding the emitter end 84 of fiber optic cable 30. FIG. 8 is an end view of an alternative partial ring shaped member embodiment 128 for holding the fiber optic cable. Embodiment 128 is adapted to extend only partially around tubular member 54 and is preferably somewhat resilient to allow opposed distal ends 130 and 132 to be pulled apart and engaged with member 54 when located in aperture 126 without requiring disassembly of the video camera head. Embodiment 128 includes the same sidewardly extending portion 78 and threaded mounting portion 80 as in member 74.

FIG. 9 shows a typical insufflator bulb 134 including a fitting 136 that can be attached to fitting 46 on endoscope head 14 for communicating air under pressure to the interior of speculum 44 via passage 112 through endoscope head 14 (FIG. 5).

Thus there has been shown and described a video endoscope with interchangeable endoscope heads that fulfills all of the objects and advantages sought therefor. Many changes, modifications, variations, and other uses and applications of the present construction, will, however, become apparent to those skilled in the art after considering this specification and the accompanying drawings. All such changes, modification, variations, and other uses and applications which do not depart from the spirit and scope of the invention are deemed to be covered by the invention which is limited only by the claims which follow.

What is claimed is:

1. A video endoscope comprising:
   at least one endoscope head having an objective element adapted to receive and transmit an image of an object to be examined and a light conductive element adapted to receive light from a light source and emit the light to illuminate the object to be examined,
   a video camera head including a video camera, the video camera head being adapted to be mounted to the endoscope head to allow relative rotation of the video camera head and the endoscope head with the video camera positioned to receive the image transmitted by the objective element, and
   a member adapted to receive light from a light source and emit the light mounted for rotation about the video camera head in position to communicate light to the light conductive element when the video camera head is mounted to the endoscope head.

2. The video endoscope of claim 1 wherein the member adapted to receive light from a light source and emit the light is a fiber optic cable having a receptor end for receiving light and an emitter end for emitting the light.

3. The video endoscope of claim 2 wherein the video camera head is mountable to the endoscope head so as to allow unlimited relative rotation therebetween and the fiber optic cable is mounted for unlimited rotation about the video camera head.

4. The video endoscope of claim 2 wherein the fiber optic cable is mounted alongside the exterior of the video camera head.

5. The video endoscope of claim 4 wherein the video camera head further comprises an annular shaped outer portion and a member mounted for rotation about the annular outer portion, the member being adapted for holding the emitter end of the fiber optic cable in position to communicate light to the light conductive element when the video camera head is mounted to the endoscope head.

6. The video endoscope of claim 5 wherein the light conductive element includes a receptor end having an aperture adapted for receiving the emitter end of the fiber optic cable and the member for holding the fiber optic cable holds the emitter end of the fiber optic cable in position for insertion into the aperture when the video camera head is mounted to the endoscope head.

7. The video endoscope of claim 1 wherein the video camera includes a fitting for the operative connection of a video cable thereto.

8. The video endoscope of claim 1 wherein the at least one endoscope head includes an endoscope head including an objective element that is a rod lens.

9. The video endoscope of claim 8 wherein the rod lens is sized for insertion into the ear and the endoscope head is adapted to receive a speculum having an interior portion in overlaying relation to the rod lens.

10. The video endoscope of claim 9 wherein the endoscope head further comprises a fitting for the attachment of an insufflator bulb and a passage adapted for communicating air under pressure from the insufflator bulb to the interior of the speculum.

11. The video endoscope of claim 1 further comprising means manually adjustable for focusing the image transmitted to the video camera.

12. A video endoscope comprising:

a video camera head including a video camera, at least one endoscope head having a rod lens for receiving and transmitting an image of an object to be examined and a light conductive element for receiving light from a light source and emitting the light for illuminating the object to be examined, the video camera head being detachable mountable to the endoscope head in position such that an image transmitted by the objective element of the endoscope head will be received by the video camera of the video camera head, a fiber optic cable having a receptor end for receiving light from a light source and an emitter end for emitting light from the light source, and the video camera head further including an annular shaped outer portion and a member mounted to the video camera head around the annular outer portion, the member being adapted for holding the fiber optic cable with the emitter end positioned to communicate light to the light conductive member of the endoscope head when the video camera head is mounted to the endoscope head and allowing rotation of the video camera head in the member and rotation of the member about the video camera head.

13. The video endoscope of claim 12 wherein the light conductive element includes a receptor end having an apeme adapted for receiving the emitter end of the fiber optic cable and the member for holding the fiber optic cable holds the emitter end of the fiber optic cable in position for insertion into the aperture when the video earnera head is mounted to the endoscope head.

14. The video endoscope of claim 12 wherein the video camera head and the endoscope head include fittings cooperatively engageable for detachably mounting the video camera head to the endoscope head, the member for holding the fiber optic cable holding the emitter end thereof in predetermined relation to the video camera head fitting, and the light conductive element including a portion for receiving light located in corresponding relation to the endoscope head fitting such that when the video camera head is mounted to the endoscope head the emitter end of the fiber optic cable can be positioned for communicating light to the light receiving portion.

15. The video endoscope of claim 14 wherein the fittings allow relative rotation between the video camera head and the endoscope head when cooperatively engaged.

16. The video endoscope of claim 14 wherein one of the fittings includes detent members releasably engageable with the other fitting when the fittings are cooperatively engaged.

17. A video endoscope comprising:

a video camera head including a video camera, at least one endoscope head having a rod lens including a distal rod end for receiving an image of an object to be examined and a rear aperture for transmitting the image, and a light conductive member including a receptor end portion adapted for receiving light and an emitter end portion in the distal rod end of the rod lens for emitting the light for illuminating the object to be examined, fittings on the video camera head and on the endoscope head cooperatively engageable for removably mounting the video camera head to the endoscope head such that an image transmitted through the aperture of the endoscope head will be received by the video camera of the video camera head, a fiber optic cable having a receptor end for receiving light from a light source and an emitter end for emitting light from the light source, and a member on the video camera head adapted for holding the fiber optic cable such that when the video camera head is mounted to the endoscope head the emitter end of the fiber optic cable will be positioned in communication with the light receptor end portion of the endoscope head, the fittings allowing relative rotation of the endoscope head and the video camera head when mounted thereto and the member for holding the fiber optic cable allowing relative rotation between the video camera head and the fiber optic cable.

18. The video endoscope of claim 18 wherein the video camera includes a fitting for the operative connection of a video cable thereto.

* * * * *

UNITED STATES PATENT AND TRADEMARK OFFICE
CERTIFICATE OF CORRECTION

PATENT NO. : 5,682,199
DATED : October 28, 1997
INVENTOR(S) : James D. Lankford

It is certified that error appears in the above-identified patent and that said Letters Patent is hereby corrected as shown below:

Col. 3, line 50, "carded" should be -- carried -- .
Col. 7, line 52, "earnera" should be -- camera -- .
Col. 8, line 20, "fie" should be -- the -- .
Col. 9, line 6, "a/so" should be -- also -- .
Col. 11, line 36, "apeme" should be -- aperture -- .
Col. 11, line 40, "earnera" should be -- camera -- .
Col. 12, line 43, "18" should be -- 17 -- .
Col. 8, line 33, "time:" should be -- time. -- .

Signed and Sealed this

Twenty-third Day of December, 1997

Attest:

BRUCE LEHMAN

*Attesting Officer*           *Commissioner of Patents and Trademarks*